(12) United States Patent
Zheng

(10) Patent No.: US 7,807,386 B2
(45) Date of Patent: *Oct. 5, 2010

(54) PEPTIDES FOR DISCRIMINATION OF PRIONS

(75) Inventor: Jian Zheng, Raritan, NJ (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/357,888

(22) Filed: Jan. 22, 2009

(65) Prior Publication Data

US 2009/0136967 A1 May 28, 2009

Related U.S. Application Data

(62) Division of application No. 11/229,960, filed on Sep. 19, 2005, now Pat. No. 7,482,172.

(60) Provisional application No. 60/614,533, filed on Sep. 30, 2004.

(51) Int. Cl.
*G01N 33/53* (2006.01)
*G01N 33/543* (2006.01)
*G01N 33/566* (2006.01)
*C07K 14/00* (2006.01)

(52) U.S. Cl. .................. 435/7.1; 436/501; 436/518; 530/300

(58) Field of Classification Search ................ None
See application file for complete search history.

(56) References Cited

U.S. PATENT DOCUMENTS 7,482,172 B2 * 1/2009 Zheng .................. 436/518
2002/0004586 A1 * 1/2002 Aguzzi .................. 530/388.2

FOREIGN PATENT DOCUMENTS

WO    WO/02/065133    *   8/2002

OTHER PUBLICATIONS

Luo et al. Molecular modeling and deletion mutagenesis implicate the nuclear translocation sequence in structural integrity of fibroblast growth factor-1. J Biol Chem. 1996. 271(43): 26876-83.*

Chon and Chaikof. Soluble heparin-binding peptides regulate chemokinesis and cell adhesive forces. Am J Physiol Cell Physiol. 280: C1394-C1402, 2001.*

* cited by examiner

*Primary Examiner*—Zachariah Lucas
*Assistant Examiner*—Michelle Horning

(57) ABSTRACT

The aim of the present invention is to provide a non-intrusive way to isolate, concentrate and monitor the TSE disease-related pathogenic prion protein. The invention described several peptides and their ability to capture $PrP^{Sc}$ from brain homogenate of prion disease infected animal and human. These eight peptides do not capture cellular prion protein from individual with no prion disease.

4 Claims, 3 Drawing Sheets

Figure 1: IP capture and immunoblot of hamster PrP$^{Sc}$

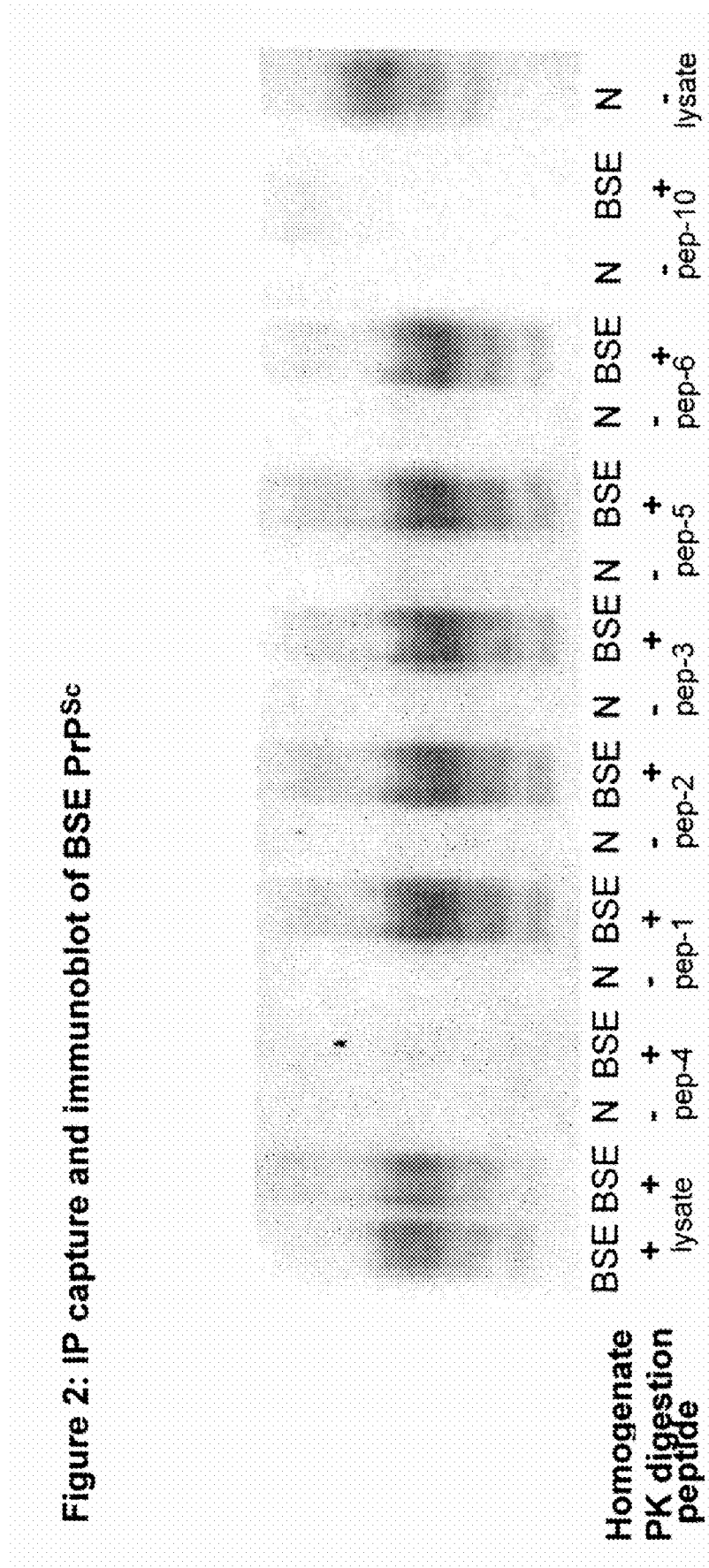

Figure 3. Immunocapture of PrP$^{Sc}$ from brains of vCJD by peptides

| Homogenate | LBD | vCJD | LBD | vCJD | LBD | vCJD | LBD | vCJD | LBD | vCJD | LBD | vCJD |
|---|---|---|---|---|---|---|---|---|---|---|---|---|
| PK digestion | − | + | − | − | − | − | − | − | − | − | − | − |
| peptide | lysate | lysate | 1 | 2 | 3 | lysate | 1 | 2 | 3 | 5 | 6 | 5 | 6 |

SEQUENCE LISTING

<160> NUMBER OF SEQ ID NOS: 10

<210> SEQ ID NO 1
<211> LENGTH: 8
<212> TYPE: PRT
<213> ORGANISM: Homo sapiens

<400> SEQUENCE: 1

Trp Gln Pro Pro Arg Ala Arg Ile
1               5

<210> SEQ ID NO 2
<211> LENGTH: 13
<212> TYPE: PRT
<213> ORGANISM: Homo sapiens

<400> SEQUENCE: 2

Asn Trp Cys Lys Arg Gly Arg Lys Gln Cys Lys Thr His
1               5                   10

<210> SEQ ID NO 3
<211> LENGTH: 7
<212> TYPE: PRT
<213> ORGANISM: Homo sapiens

<400> SEQUENCE: 3

Asn Tyr Lys Lys Pro Lys Leu
1               5

<210> SEQ ID NO 4
<211> LENGTH: 14
<212> TYPE: PRT
<213> ORGANISM: Homo sapiens

<400> SEQUENCE: 4

Lys Asp Phe Leu Ser Ile Glu Leu Val Arg Gly Arg Val Lys
1               5                   10

<210> SEQ ID NO 5
<211> LENGTH: 12
<212> TYPE: PRT
<213> ORGANISM: Homo sapiens

<400> SEQUENCE: 5

Tyr Arg Gly Tyr Arg Gly Tyr Arg Gly Tyr Arg Gly
1               5                   10

<210> SEQ ID NO 6
<211> LENGTH: 15
<212> TYPE: PRT
<213> ORGANISM: Homo sapiens

<400> SEQUENCE: 6

Tyr Arg Gly Arg Tyr Gly Tyr Lys Gly Lys Tyr Gly Tyr Arg Gly
1               5                   10                  15

```
<210> SEQ ID NO 7
<211> LENGTH: 21
<212> TYPE: PRT
<213> ORGANISM: Homo sapiens

<400> SEQUENCE: 7

Ala Gln Lys Lys Asp Gly Lys Lys Arg Lys Arg Ser Arg Lys Glu Ser
1               5                   10                  15

Tyr Ser Ile Tyr Val
            20

<210> SEQ ID NO 8
<211> LENGTH: 21
<212> TYPE: PRT
<213> ORGANISM: Homo sapiens

<400> SEQUENCE: 8

Ala Arg Thr Lys Gln Thr Ala Arg Lys Ser Thr Gly Gly Lys Ser Pro
1               5                   10                  15

Arg Lys Gln Leu Ala
            20

<210> SEQ ID NO 9
<211> LENGTH: 23
<212> TYPE: PRT
<213> ORGANISM: Homo sapiens

<400> SEQUENCE: 9

Ser Gly Arg Gly Lys Gly Gly Lys Gly Leu Gly Lys Gly Gly Ala Lys
1               5                   10                  15

Arg His Arg Lys Val Leu Arg
            20

<210> SEQ ID NO 10
<211> LENGTH: 12
<212> TYPE: PRT
<213> ORGANISM: Homo sapiens

<400> SEQUENCE: 10

Thr Ile Ala Asp Arg Tyr Tyr Arg Glu Thr Ala Arg
1               5                   10
```

PEPTIDES FOR DISCRIMINATION OF PRIONS

CROSS REFERENCE TO RELATED APPLICATIONS

This application is a divisional of U.S. application Ser. No. 11/229,960, filed Sep. 19, 2005, now U.S. Pat. No. 7,482,172, which claims the benefit of U.S. Provisional Application No. 60/614,533, filed Sep. 30, 2004. The contents of each of these applications are hereby incorporated by reference.

BACKGROUND

Prion diseases or transmissible spongiform encephalopathies (TSE) have captured the interest of the scientific community, not only because they challenged conventional thought about the nature of infectious agents, but also because of the potentially serious public health threat they pose to food and blood safety. Furthermore, the possibility of disease transmission between animals and humans has been dramatically underscored in recent years by the epidemic occurrence of a new variant disease form, vCJD. The present invention described the use of synthetic peptides for the diagnosis of Transmissible Spongiform Encephalopathies (TSE) diseases in animals and humans.

Prions—A Pathogenic Agent Causing TSE

Transmissible spongiform encephalopathies (TSEs) comprise a group of rapidly progressing, neurodegenerative fatal diseases that affect both humans and animals. TSEs have clinical and neuropathological characteristics which include devastating dementia, pyramidal and extrapyramidal signs with myoclonus, multifocal spongiform changes, astrogliosis, amyloid plaques, neuronal loss, absence of inflammatory reaction and are usually characterized by a long incubation period.

It was once suggested that TSE diseases might be caused by "slow viruses" or viroids (Gajdusek 1977). However, the extreme resistance of scrapie infectivity to radiation, nucleases, and other reagents damaging to genetic materials are inconsistent with the "virus" theory. All these "unusual" characteristics of the TSE infectious agent led Dr. Stanley Prusiner to propose the concept of "prions" in 1982 (Prusiner 1982). Prion (PrP), which stands for nucleic acid-free proteinaceous infectious particle, is a glycoprotein present in humans and animals. The cellular form of this protein (PrP$^C$) has two N-link glycosylation sites and a GPI anchor at the C-terminus. It has been most commonly found in neurons, and, to a much lower extent, it has also been found in other cells such as leucocytes, monocytes and platelets (Holada 2000). The transmissible scrapie disease form of the prion protein (PrP$^{Sc}$) is a protease resistant isoform of its cellular precursor and is predominantly found in brain. At much lower level, it has also been found in tonsil, spleen, and lymph nodes in vCJD patients (Parizek 2001). As a result of Prusiner's concept of the "prion" as an infectious agent responsible for scrapie disease, and by extension, that of all TSE diseases gave rise to the notion of what are commonly referred to as Prion diseases to describe a class of pathologies believed to be linked to this protein.

Human prion disease is known as Creutzfeldt-Jakob disease (CJD) and usually affects elderly persons. Depending on disease phenotype, sporadic (sCJD) accounts for most of CJD, while about 10% are familial CJD (fCJD). Only recently, a new variant of CJD (vCJD) has emerged which occurs in young adults. Since 1995, more than 100 cases have been reported. Prion diseases affect many species of domestic and wild animals, manifestations of which are often given unique names, for example, scrapie in sheep and goats (McGowan 1922), chronic wasting disease (CWD, Williams 1980) in cervids and bovine spongiform encephalopathy (BSE, or "mad cow" disease, Wells 1987) in cattle.

Characteristics of PrP$^C$ and PrP$^{Sc}$

According to the Prusiner's "protein only" hypothesis, the transmissible pathogen causing prion diseases is a protein. The major component of the prion appears to be abnormally folded PrP, designated as PrP$^{Sc}$ (disease-specific, "scrapie" isoform). It is believed that PrP$^{Sc}$ is generated from its normal counterpart, PrP$^C$, through a change in conformation (Cohen, 1998). Although there is still ambiguity concerning the mechanism of the conversion, it is still broadly accepted that in the presence of PrP$^{Sc}$, normal PrP$^C$, acting as a substrate, undergoes a conformational structure change, and becomes PrP$^{Sc}$ through an autocatalytic process and results in PrP$^{Sc}$ aggregation and amyloid rod formation, hence causing cell death (Hope 1986, Horwich 1997). The structural change from PrP$^C$ to PrP$^{Sc}$ is most supported by a crucial conformational change, involving a substantial increase in the amount of Beta-sheet structure of the protein, with possibly a small decrease in the amount of alpha-helix, indicated by circular dichroism and infrared spectroscopy (Pan 1993, Caughey 1991). It appears that the efficiency of conversion from PrP$^C$ into PrP$^{Sc}$ depends on the degree of sequence homology between the two PrP conformers. Because this unique mechanism, prion diseases can be readily transmitted within the same species, and when the PrP sequence homology is sufficient, from species to species (Raymond, 2000). Therefore, if correct, the proposed mechanism of transmission of prion diseases provides the potential to trigger epidemics by transmission of these brain disorders between animals and humans.

Protease resistance is another characteristic that distinguishes PrP$^{Sc}$ from PrP$^C$. In cultured cells and brain or in samples from many patients with GSS, PrP$^{Sc}$ is smaller than its cellular precursor PrP$^C$. Even though cellular prion and scrapie prion are two isoform of same PRNP genomic product, PrP$^C$ is completely degraded by Proteinase K treatment while PrP$^{Sc}$ undergoes only limited digestion. The digestion yields a form of protein referred to as PrP 27-30 in which the N-terminus has been removed. PrP 27-30 has been postulated to be the PrP$^{Sc}$ core required for PrP$^C$ hosted PrP$^{Sc}$ replication. The protease treated prion molecule, PrP 27-30 or PrP$^{res}$, is tightly linked to scrapie infectivity (Gabizon 1988), and provides additional evidence that PrP$^{Sc}$ is an infectious protein.

An additional attribute, perhaps linked to the significant increase in Beta-sheet structure and concomitant protease-resistance, is the observed difference in solubility between PrP$^{Sc}$ and PrP$^C$. While PrP$^C$ is a soluble protein, the PrP$^{Sc}$ isoform is highly insoluble. Furthermore, PrP$^C$ is found attached to the surface of neurons through a GPI tail anchored into membrane (Shyng 1994) while PrP$^{res}$ is found in the cytoplasm of affected cells (Taraboulos 1990), most likely associated with late endosomal and lysosomal compartments (Arnold 1995), and PrP$^{Sc}$ is also localized in amorphous aggregates in enriched fractions from infected brain (Meyer 1986).

There is mounting evidence indicating a tight linkage between scrapie infectivity and PrP 27-30. Even in the purest samples, the estimated ratio of PrP molecules to infectious units is ~$10^4$ to $10^5$ (Horwich 1997, Bolton 2001). At such low levels of infectivity, it is possible that other components, co-factors, or covalent modifications, are required for infectivity. The transgenic studies on the susceptibility of mice expressing chimeric human-mouse $PrP^C$ suggest the presence of at least one host factor other than $PrP^C$, tentatively termed factor X, which might function as a molecular chaperone in the formation of $PrP^{Sc}$ (Telling 1995).

Infectivity and Transmissibility of Prion Diseases

Prion diseases are transmissible. The transmissibility of animal prion diseases has long been established experimentally by inoculation of brain homogenates from affected animals into healthy ones, such scrapie from sheep to sheep (Cuillé 1936) and across species to goat (Pattison 1957), kuru and CJD from humans to chimpanzees (Gajdusek 1966, Gibbs 1968), The significant breakthrough was the successful transmission of scrapie to mice (Chandler 1961) which greatly facilitated TSE research by providing an experimental model. The cause of recent BSE in cattle and new variant CJD in human (vCJD) was considered a consequence of dietary exposure to the mix of scrapie sheep carcasses rendered for animal feed in the case of BSE (Brown 1997) and to beef from cattle affected with BSE in the case of vCJD (Bruce 1997). The link between vCJD and BSE is further supported by the neuropathologic evidence obtained from BSE-adapted macaques, the nearest model to humans, and from the study on inbred mice inoculated with the agent causing BSE and VCJD (Lasmézas 1996). Of particular concern to an epidemic expanding of CWD in mule deer and elk in North America is whether CWD, like BSE, could be transmitted to humans who may be exposed to the disease through hunting, or handling and eating infected meat. Tragic, unintended transmission of prion disease in humans has been documented, such as the kuru epidemic caused by cannibalistic ingestion of brain tissue from the deceased, and the iatrogenic transmission of CJD through the use of hormones, tissue transplants, and contaminated medical devices.

There is no hard evidence indicating any of CJD diseases is related to animal TSEs that may have crossed species barriers. The epidemic of kuru has provided the largest body of evidence of acquired human prion disease. Although no vCJD patient has been documented as a victim of human-to-human transmission, the close link between BSE and vCJD attracted considerable attention. Concerns about human infection have been based on the observation that $PrP^{Sc}$ is readily detectable in BSE and vCJD lymphoreticular tissues but not in classic CJD (Hill 1997), followed by the presumption that scrapie pathogen from sheep passage to cattle may have altered host range and become more adaptable to human. Experimental precedents for such behavior are well known: passage of mouse-adapted strains of scrapie through hamsters altered their transmissibility on back passage to mice (Kimberlin 1987, Kimberlin 1989); human strains of kuru or CJD did not transmit to ferrets or goats until passaged through primates or cats (Gibbs 1979); and a bovine strain of BSE did not transmit to hamsters until passaged through mice (Foster 1994). Alternatively, if BSE originated from a spontaneous mutation in cattle, experimental studies of species susceptibility to this new strain of transmissible spongiform encephalopathy (TSE) had not sufficiently advanced to predict that humans would not be susceptible.

Study on human CJD and vCJD disease indicated that genomic susceptibility might yet be another factor that may influence the spread of TSE in humans. The majority of sporadic CJD patients were found to be homozygous for Met/Met or for Val/Val at codon 129 (Belay 1999). Nevertheless, all reported vCJD cases have been found to be homozygous for Met/Met.

The size and duration of vCJD epidemic still remains uncertain. Depending on the assumptions made and the modeling calculations employed, different predictions were proposed. One estimation of total vCJD predicts as few as 205 cases (Valleron 2001). On the other hand, another prediction for vCJD mortality for the next 80 years ranges from 50 to 50,000 if infection comes only from BSE. It could reach up to 150,000 if BSE is proven to infect sheep and if subsequently it is allowed to enter human food chain (Ferguson 2002). Although it is impossible to make accurate predictions if the necessary parameters are either mistaken or not available, one thing is certain that if vCJD infectivity is present in blood, any prediction will be an underestimate. In addition, vCJD has been proven to be a new disease entity and not simply the result of increased surveillance of CJD in humans (Hillier 2002).

Countermeasures have been taken by government to eliminate the spread of BSE incidence. Ruminant protein feed was banned in US and UK (1988). A series of measures have also been taken to prevent potentially infected meat from entering human food chain. To further reduce the human risk, FDA and CBER has issued a new policy in August 2001, which indefinitely defers any donor who stayed cumulative $\geqq 6$ month during 1980-1996 in the United Kingdom (FDA 2001).

Diagnostic Assay for Prion Disease

The development of sensitive and reliable assays for prion detection is absolutely essential for disease surveillance, risk assessment, and when combined with future therapeutics, for disease prevention and eradication. Currently, there are basically three assay formats for diagnosis of prion diseases. (1) Animal infectivity bioassays are by far the most sensitive method for the measurement of infectious prion in experimental scrapie in rodents, usually accomplished by intracerebral injection of brain homogenates from sick animals into recipient animals. However, the quantitative measurement of prion disease infectivity in different animal species is limited due to the "species barrier" and distinct prion "strains" exist that differ in terms of pathology, incubation time, and molecular characteristics of $PrP^{Sc}$. Therefore, this time-consuming, expensive postmortem diagnosis is mostly used as a research tool for distinguishing different prion strains in rodents, and serves as a reference for calibration of infectious brain material. (2) Current PrP Immunoassays are based on the detection of protease-resistant $PrP^{Sc}$, the only known molecular hallmark of all prion diseases. For many years, the detection of $PrP^{Sc}$ by immunochemical methods (immunohistochemistry and Western blotting) has provided the most accurate diagnosis for prion diseases in animals and humans (Schaller 1999, Biffiger 2002). They are widely used for postmortem diagnosis. Many monoclonal and polyclonal antibodies have been raised against various regions of PrP for this purpose such as widely used 3F4, 6H4 described in U.S. Pat. No. 4,806,627 and EP0861900. However, only few were claimed to be able to discriminate between $PrP^C$ (often present in much larger quantities) and $PrP^{Sc}$. Monoclonal antibodies reported by Korth in 1997 and by Paramithiotis in 2003 were both IgMs and no diagnosis assay was developed by these antibodies. Consequently, almost all current immunochemical methods require a step to reduce or eliminate a $PrP^C$, usually by nonspecific proteolysis such as proteinase K (PK) digestion, prior to the detection of $PrP^{Sc}$. Such pretreatment cleaves the first 60-70 residues from $PrP^{Sc}$ to yield a PK-resistant PrP27 kDa-30 kDa core called $PrP^{res}$. Anti-PrP antibodies that recognize the remaining C-terminal region of the protein can then be used to detect the N-terminally truncated $PrP^{Sc}$, or $PrP^{res}$, present only in pathological samples.

For immunohistochemical staining, tissue sections are also pretreated, usually by acid hydrolysis to reduce the $PrP^C$ related background. Therefore, $PrP^{res}$ is a surrogate for the precursor $PrP^{Sc}$ in these immunoassays. Among the various immunoassay formats, Western blotting has the advantage of revealing detailed molecular patterns of PrP based on the migration of di-, mono- and unglycosylated PrP bands. This method also has been widely used for distinguishing distinct brain $PrP^{res}$ subtypes in human and animal prion diseases. Besides Western blot, other assay formats have now been developed for higher sample throughput, increased sensitivity, and better quantification, including traditional ELISA, dissociation-enhanced lanthanide-fluorescence-immunoassay (DELFIA, Barnard 2000 and a method described in US20020137114A1) and conformation-dependent immunoassay (CDI) combined with ELISA and fluorescence detection (Safar 1998, US 20010001061A1, US20020001817A1). However, regardless of the format, $PrP^{Sc}$ can be differentiated from $PrP^C$ only after the mandatory PK digestion, which may be difficult to optimize for disparate biological samples. (3) Other methods have also been described for sample treatment including immunohistochemistry of third eyelid lymphoid tissue for preclinical diagnosis of ovine scrapie (O'Rourke 2000, U.S. Pat. Nos. 6,165,784, 6,261,790), chemical treatment with sodium phosphotungstate to enrich $PrP^{Sc}$ from brain and from other peripheral tissue homogenates (Wadsworth 2001), and detection of a new isoform of the prion protein in the urine of infected animals and humans (Shaked 2001b, WO0233420A2). Other detection systems were also documented including capillary electrophoresis, and Fourier transform infrared spectroscopy. These methods are still in their initial stages of development and are technically complex. In addition to the traditional identification of pathogenic prion by eliminating cellular prion followed by non-discriminatory anti-prion antibody recognition, other reagents were found to be able to differentiate $PrP^{Sc}$ from $PrP^C$, such as plasminogen and fibrinogen. The evidence provided suggested that a property common to $PrP^{Sc}$ of various species, rather than prion primary sequence or the specific tertiary structure of individual $PrP^{Sc}$ molecules, could be responsible for binding to plasminogen (Fischer 2000, Maissen 2001). The application for the use of plasminogen and other serum/plasma proteins for the capture and detection of pathogenic prion protein has been described in WO0200713 and in US20010053533A1 (Aguzzi 2001).

All current manufactured prion diagnosis assays use brain tissue as a sample source. The European Commission in 1999 evaluated 4 BSE test kits from different manufacturers (Moynagh 1999). They all required a separate sample preparation procedure. Depending on the kit instructions, the brain tissue homogenate needed to be processed, including denaturation, PK digestion or $PrP^{Sc}$ enrichment. The assay detection systems employed in DELFA, immunoblot, or in plate ELISA formats used either chemiluminescent or a calorimetric substrate.

Challenges to Antemortem Diagnosis of Prion Disease

An issue common to $PrP^{Sc}$-based antemortem assays is whether $PrP^{Sc}$ is present in peripheral tissues or body fluids. Because of technical difficulties, little experimental data on the presence of $PrP^{Sc}$ or its associated infectivity in body fluids are available, and this subject remains controversial. In the hamster model of scrapie, a low level of infectivity can be detected in blood. Although the infectivity in lymphocyte-rich buffy-coat derived from diseased hamster blood is greater than in plasma, it only accounts for relatively a small portion when compared to whole blood inoculums. The molecular definition of this infectious agent present in the blood is not clear. Searching for risk factors and possible sources of infection in sporadic CJD patients revealed no significant correlation of disease to diet, blood transfusion or receiving other blood product. Although early reports indicated the possible presence of infectivity in blood obtained from CJD patients after intracerebral inoculation to mice (Manuelidis 1985, Tateishi 1985), The highest amount of infectivity or $PrP^{res}$ is invariably found in the central nervous system (CNS), but not consistently found in peripheral tissues in classical human prion diseases, except in the case of vCJD. The presence of readily detectable $PrP^{Sc}$ in the peripheral lymphoreticular tissues such as tonsils, spleen, and lymph nodes of vCJD patients has raised a serious concern that abundant amounts of $PrP^{res}$ present in lymphoreticular tissues could interact with the circulatory system, and as a consequence, trace amounts of $PrP^{Sc}$ may be present in blood of vCJD patients for possible blood transmission. Other TSE infectivity in blood has also been demonstrated in various experimental animals. Most blood for infectivity studies was obtained from TSE-adapted rodents such as mice and hamsters. Mice-adapted BSE, mice-adapted vCJD has been established through intracerebral and intravenous transmission. The only exception model was a study conducted in the sheep. In this experiment, a sheep transfused with whole blood, taken from another sheep inoculated with BSE brain lysate, developed symptoms of BSE (Houston 2000, Hunter 2002). However, these experimental results yet need to be fully evaluated. It is anticipated that finding of such infectious agent in blood would help us to better understand the relationship between $PrP^{Sc}$ and TSE disease.

It is important to note that the harsh sample treatment to eliminate $PrP^C$ background may not be suitable for other peripheral tissue specimens or body fluids due to differing protein content, the difficulty of applying this assay to large numbers of samples, the inevitable elimination of protease-sensitive $PrP^{Sc}$ folding intermediates or even a fraction of authentic $PrP^{Sc}$, thus reducing the sensitivity of detection. This may be especially relevant for assays using peripheral tissues and body fluids, as only low levels of $PrP^{Sc}$ may be present (Horiuchi 1999, Jackson 1999, Swietnicki 2000). These concerns necessitate the development of immunological reagents with a high affinity for $PrP^{Sc}$, allowing for specific detection without the need for proteolytic treatment.

Discovery of Novel Capture Reagent for $PrP^{Sc}$ Detection

Whether or not one accepts the "protein only" or "prion only" hypothesis, there are continuous efforts underway to search for agents or molecules other than prion that may contribute to the pathogenesis of prion disease. This search is driven by many unanswered questions. For example, synthesized prion protein, free of any contamination, does not cause disease; the mechanism that triggers the conversion of normal $PrP^C$ to the pathogenic $PrP^{Sc}$ isoform is unknown. Another unresolved question involves the various prion disease phenotypes observed in animals and humans, defined by disease incubation period, glycosylation level and lesion patterns. After serial passage in inbred mice homozygous for a single PRNP genotype, all the scrapie strains retained their original disease profile. These observations led investigators to question whether varied phenotypic strains were dominated by different conformational isoforms of same cellular prion precursor, or whether there is another factor that determines the phenotype of the inheritable strain. In fact, in vitro conversion models $PrP^{res}$ formed in cell-free reactions has never been shown to constitute new TSE infectivity in animals (Caughey 2003). These questions led many to believe that there is a missing element, dubbed "protein X" as Prusiner suggested, yet to be discovered.

The presence of a tightly bound RNA or DNA molecule in the prion particle was proposed to explain propagation of different strains of scrapie agent with distinct phenotypes in animals homozygous for the PRNP gene (Weissmann 1991). Analysis of highly purified scrapie prions by return refocusing gel electrophoresis revealed the small size of remaining nucleic acids (Kellings 1992). In a recent report, however, Narang indicated that animals inoculated with ssDNA purified from scrapie-hamster brains mixed with non-pathogenic prion developed clinical disease (Narang 2002). Based on his findings, he postulated that the "accessory protein" coded by the ssDNA may be involved in $PrP^C$ to $PrP^{Sc}$ conversion. Based on those in vitro conformation and conversion studies, it was hypothesized that DNA would act as a guardian of the $PrP^{Sc}$ conformation as well as a catalyst to facilitate $PrP^{Sc}$ conversion and aggregation (Cordeiro 2001). Most recently, it was reported that stoichiometric transformation of $PrP^C$ to $PrP^{res}$ in vitro requires specific RNA molecules (Deleault 2003). The anti-nucleic acid monoclonal antibody developed by Ortho-Clinical Diagnostics that can discriminatively capture $PrP^{Sc}$ but not $PrP^C$ (U.S. 60/434,627, U.S. 60/446,217) is another evidence to demonstrate the association of $PrP^{Sc}$ to nucleic acids.

It is known that $PrP^{Sc}$ isolated from diseased brain is also associated with a variety of glycans. Those include 1,4-linked glucose units in prion rods, sphingolipids, polysaccharides and other membrane components in $PrP^{Sc}$ aggregates (Appel 1999, Klein 1998), and sulfated proteoglygan in prion amyloid plaques (Snow 1990), a property that has been exploited in immunohistochemistry, where binding by heparan sulfate antibodies (anti-HS) and heparan sulfate proteoglycan antibodies (anti-HSPG), has been shown to correlate with abnormal PrP as early as 70 days post-infection and throughout the course of the disease (McBride 1998). Through a mechanism that is perhaps different from that by which nucleic acids participate in the conversion of $PrP^C$ to $PrP^{Sc}$, glycan also convert cellular prion protein into Beta-sheet conformation. In vitro conversion from $PrP^C$ to $PrP^{Sc}$ and in prion infectivity reconstitution experiments, sulfate glycans have been shown either to facilitate the conversion or to escalate infectivity (Wong 2001, Shaked 2001a, Diaz-Nido 2002). With recombinant GST::full-length prion and GST::prion fragment, Warner recently demonstrated direct binding of recombinant prion to heparin and heparan sulfate (Warner 2002). The peptide region 23-52 in prion sequence was positive in all HS and HSPG binding tests. Since the peptide failed to compete with full-length prion for binding to heparin, the author suggested that there might be another major GAG-binding site in intact $PrP^C$. Another interesting observation is that plasminogen has been reported to bind brain-derived $PrP^{Sc}$, but not to $PrP^C$. Although it has not been demonstrated that plasminogen has a direct interaction with $PrP^{Sc}$, a binding site is suggested within the Kringle region of plasminogen, a region that has a known affinity for heparin. Another noteworthy observation is that GAGs from different species (bovine and porcine) or from different organs (lung, kidney and intestine) have shown different affinities for prion binding. The difference in affinity may be due to prion sequence itself, or may depend on the presence of particular sugar unit in the tested GAGs.

In light of these observations, a number of peptides were proposed that are designed to selectively capture $PrP^{Sc}$ but not $PrP^C$ through peptide affinity to unique $PrP^{Sc}$ conformation or to $PrP^{Sc}$ associated molecules. They were screened by the ability to identify and to capture $PrP^{Sc}$ from homogenates of diseased brains by immunoprecipitation without protease pretreatment.

(1) Heparin/heparin Sulfate Binding Domain Peptides:

Glycans (GAG) such as heparin and heparin sulfate were associated with $PrP^{Sc}$ amyloid aggregates. Because the association affinity was much higher in $GAG::PrP^{Sc}$ than in $GAG::PrP^C$ it is possible to use peptides characterized as glycan binding domain to selectively capture $PrP^{Sc}$ but not $PrP^C$. For this reason, peptides described as heparin or heparin sulfate binding domain were synthesized: SEQ ID NO:1: WQPPRARI of carboxy-terminal fibronectin (Woods 1993, Hines 1994); SEQ ID NO:2: NWCKRGRKQCKTH of amyloid protein precursor (Small 1994); SEQ ID NO:3: NYKKPKL of N-terminal fibroblast growth factor (FGF)-1 (Lou 1996); and SEQ ID NO:4: KDFLSIELVRGRVK of the C-terminal G-domain of the laminin alpha1 chain (Yoshida 1999).

(2) "Condensed" Kringle Peptides:

Kringle region was involved in the selective binding of plasminogen to $PrP^{Sc}$. It was also known that Kringle region had heparin/heparin sulfate binding activity (Mizuno 1994) for which positively charged amino acids (such as Arg and Lys) were involved (Soeda 1989). In a separate publication, two conserved tripeptides "YYR", or rather three discontinued "YYX" in prion sequence as suggested, were found to interact with $PrP^{Sc}$ but not interact with $PrP^C$ (Paramithiotis 2003, WO0078344A1). Interestingly found in human plasminogen sequence, there were four Tyr-Arg-Gly sequences in four out of five Kringle regions. Y(92)R(93)G(94) in Kringle region 1, Y(264)R(265)G(266) in Kringle region 3, Y(366)R(367)G(368) in Kringle region 4 and Y(470)R(471)G(472) in Kringle region 5; there were sixteen Tyr-Lys or Arg-Tyr or Lys-Tyr or Arg-Lys or Lys-Arg or Lys-Lys sequences in plasminogen such as K(19)K(20), R(61)K(62), K(77)K(78), R(153)Y(154), K(211)K(212), K(233)R(234), K(311)R(312), K(377)K(378), K(433)K(434), K(473)R(474), R(530)K(531), K(556)K(557), Y(614)K(615), R(644)K(645), R(712)Y(713), K(752)Y(753). Furthermore, several distant Tyr, Arg or Lys residues were brought closely together by disulphide bridges formed in Kringle loops. Based on these observations, it was postulated that amino acids Tyr, Arg and Lys in plasminogen Kringle region and in prion sequence, possibly through an interaction to glycan that was associated with $PrP^{Sc}$ complex, could be accounted for the selective binding to $PrP^{Sc}$. For this reason, two "condensed Kringle" peptides, SEQ ID NO:5: YRGYRGYRGYRG and SEQ ID NO:6: YRGRYGYKGKYGYRG, were synthesized.

(3) Nucleic Acid Binding Peptides:

Nucleic acids are another category of molecules that associated with $PrP^{Sc}$ aggregates. Anti-DNA antibodies have been used effectively to capture $PrP^{Sc}$. Histones are a group of proteins known to bind nuclear DNA. Therefore, three peptides, SEQ ID NO:7: AQKKDGKKRKRSRKESYSIYV of H2B(21-41); SEQ ID NO:8: ARTKQTARKSTGGK-SPRKQLA of H3(1-21); and SEQ ID NO:9: SGRGKG-GKGLGKGGAKRHRKVLR of H4(2-24), were synthesized to evaluate their ability of the capture of $PrP^{Sc}$.

SUMMARY OF THE INVENTION

The aim of the present invention is to provide a non-intrusive way to isolate, concentrate and monitor the TSE disease-related pathogenic prion protein. The invention describes several peptides and their ability to capture $PrP^{Sc}$ from brain homogenate of prion disease infected animal and human. These eight peptides do not capture cellular prion protein from individual with no prion disease. The evidence provided in support of this invention demonstrated that PrP$^{Sc}$ is associated with high affinity to many other molecules such as nucleic acid and glycans as investigated. The evidence also demonstrated that the association was strong, resistant to PK digestion treatment, and that PrP$^{Sc}$ could be readily isolated by peptides through recognition of such associated binding partner.

This invention relates to the use of described peptides to capture PrP$^{Sc}$ through glycans or nucleic acids associated with high affinity to PrP$^{Sc}$, in combination with any prion sequence-specific antibody for the detection of PrP$^{Sc}$.

In another aspect, this invention relates to the peptides, as described above, that preferably binds to pathogenic prion protein but not to the normal cellular form of prion protein.

In another aspect, this invention relates to the peptides, as described above, for the detection of PrP$^{Sc}$ through high affinity recognition of associated glycans or nucleic acids in combination of prion sequence specific antibodies.

In another aspect, this invention relates to the peptides, as described above, for the isolation, purification, capture, elimination and monitoring PrP$^{Sc}$ in biological reagent production.

In another aspect, this invention relates to compositions and kits for determining the presence of PrP$^{Sc}$, comprising peptides, as described above, for either capture or for detection step in the assay procedure.

In another aspect, this invention relates to compositions and kits for determining the presence of PrP$^{Sc}$ antibody produced in response to high affinity associated glycans or nucleic acids as a binding partner to pathogenic prion protein.

In yet another aspect, this invention relates to anti-PrP$^{Sc}$ antibodies and their production using the said glycans or nucleic acids that can interact with and/or associate with PrP$^{Sc}$, and their use in detecting glycan::PrP$^{Sc}$ or nucleic acid::PrP$^{Sc}$ complex and prion disease infection.

In another aspect, this invention relates to a non-harsh sample treatment procedure involving glycanase or nuclease digestion for the benefit of the use of described peptides as described above.

BRIEF DESCRIPTION OF THE DRAWINGS

Figure 1:
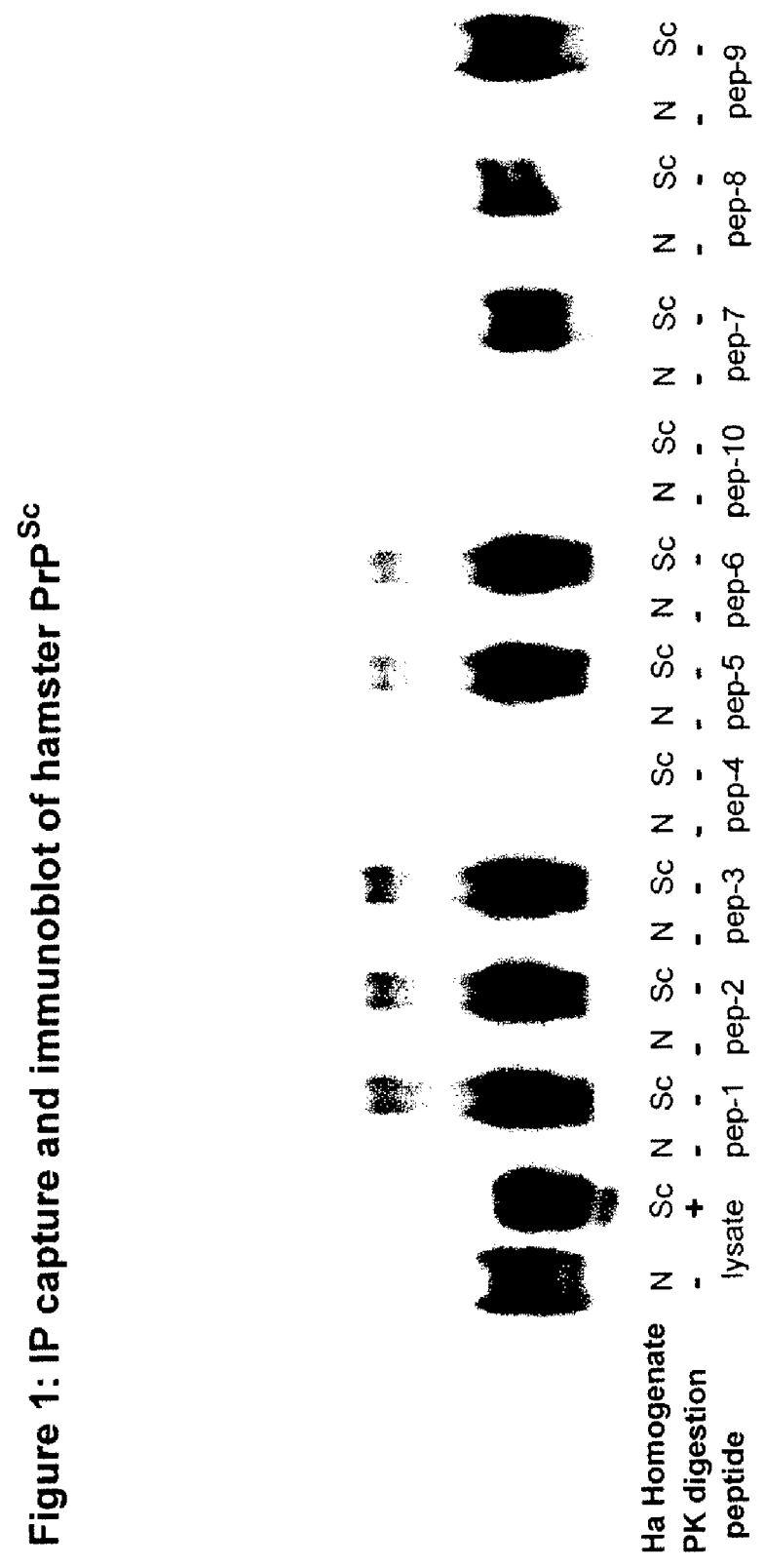

FIG. 1 is an illustration of an IP capture and immunoblot of hamster PrP$^{Sc}$. Normal (4 µl) and scrapie (3 µl) hamster brain homogenate were either directly loaded on gel or subjected to immunoprecipitation using streptavidin magmatic beads conjugated with biotinylated peptide. PrP was detected by immunoblot using 3F4. Scrapie lysate was PK digested for direct loading. Homogenate for IP capture was not PK treated.

FIG. 2 is an illustration of an IP capture and immunoblot of BSE PrP$^{Sc}$. Brain homogenate from normal cattle (10 µl) or from BSE (5 µl) was added in 1 ml IP buffer, subject to peptide-beads immunoprecipitation. The immunoprecipitated PrP was then treated with PK and analyzed by SDS-PAGE and immunoblot, detected by 6H4. Captured PrP from BSE brain homogenate was authentic PrP$^{Sc}$ since treatment with PK (50 µg/ml for 1 h at 37° C.) generates the PK-resistant core PrP$^{res}$ fragments. The clarified brain homogenates from BSE and normal control were also incubated in the absence (−) or presence (+) of PK (50 µg/ml for 1 h at 37° C.) and directly loaded onto SDS-gel as controls.

FIG. 3 is an illustration of immunocapture of PrP$^{Sc}$ from brains of vCJD by peptides. The peptide conjugated beads were used to immunoprecipitate PrP in 5 µl clarified brain homogenates from patients affected either by Lewy body dementia (LBD) or by VCJD. The immunoprecipitates were then analyzed by SDS-PAGE (4-12% gel) and Western blotting using anti-PrP antibody 3F4. 5 µl untreated LBD homogenate and 5 µl PK treated or untreated vCJD brain homogenate were loaded directly on SDS-gel to indicate the prion content.

Brain Homogenate Preparation:

Normal and scrapie hamster brain lysate were obtained from Baltimore Research and Education Foundation as 10% whole brain tissue homogenate in PBS (w/v). The lysate was further treated by adding 1/10 volume of 10× detergent homogenate buffer, composed of 5% sodium deoxycolate and 5% Igpal CA-630 (equivalent to NP-40) in PBS, incubating at 4 C for 1 hr., followed by centrifugation at 1000 g for 10 minutes. The resulting supernatant was collected and used in the assay.

Normal and BSE bovine brain tissue were provided by Veterinary Laboratories Agency (VLA), UK. Human vCJD and Lewy body dementia brain tissue were provided by National CJD Surveillance Unit (NCJDSU), UK. Brain tissue was processed the same way (or similar) as hamster brain homogenate preparation.

Synthetic Peptides:

Ten peptides were either synthesized by ResGen (currently a division of Invitrogen Corporation), or purchased from Upstate Group, Inc. Each peptide was labeled with biotin either on the C-terminal Lysine bearing an aminohexanoyl spacer (K(Lc)), or at the N-terminal through an aminohexanoyl spacer (AMCAP).

| Peptide ID | Peptide Sequence<br>Made by | Sequence Origin |
|---|---|---|
| SEQ ID NO: 1: | WQPPRARI GK(Lc)-Biotin<br>ResGen | Fibronectin |
| SEQ ID NO: 2 | Biotin-AMCAP-NWCKRGRKQCKTH<br>ResGen | Amyloid protein precursor |
| SEQ ID NO: 3 | Biotin-AMCAP-NYKKPKL-G<br>ResGen | Fibroblast growth factor (FGF)-1 |
| SEQ ID NO: 4 | Biotin-AMCAP-KDFLSIELVRGRVK<br>ResGen | Laminin A chain |
| SEQ ID NO: 5 | YRGYRGYRGYRG-K(Lc)-Biotin<br>ResGen | "condensed" Kringle-A |
| SEQ ID NO: 6 | YRGRYGYKGKYGYRG-K(Lc)-Biotin<br>ResGen | "condensed" Kringle-B |
| SEQ ID NO: 7 | AQKKDGKKRKRSRKESYSIYV-GGK(Lc)-Biotin<br>Upstate | Human histon 2B |

-continued

| Peptide ID | Peptide Sequence Made by | Sequence Origin |
|---|---|---|
| SEQ ID NO: 8 | ARTKQTARKSTGGKSPRKQLA-GGK(Lc)-Biotin Upstate | Human histon 3 |
| SEQ ID NO: 9 | SGRGKGGKGLGKGGAKRHRKVLR-GSGSK(Lc)-Biotin Upstate | Human histon 4 |
| SEQ ID NO: 10: | Biotin-AMCAP-TIADRYYRETAR ResGen | VP16 protein, HSV-2 |

Biotinylated peptide was dissolved in PBS at 1 mg/mL and stored at −20° C. until use.

Conjugation of Biotinylated Peptide to Streptavidin Magnetic Beads:

0.5 mL Dynabeads® M-280 Streptavidin (Dynal® Biotech, NY, USA, Cat.# 112.06) were washed twice with PBS and the beads isolated from buffer with the magnet (Dynal® Magnetic Particle Concentrator, MPC). 100 ug peptide and 1 mL PBS was added to the washed beads. Incubation with rotation was performed at 37 C for 1-2 hours. The beads were isolated from the buffer with the MPC, washed twice with 1 ml PBS (0.1% BSA), and rotated for 5 minutes at room temperature while washing. The peptide-conjugated beads were then blocked for 2 hours, 37° C. with 1 mM Biotin in 0.2 M Tris-HCl, pH 8.0, containing 0.1% BSA. The beads were subsequently washed 2 times with 1 ml PBS (0.1% BSA) and once with 1 ml PBS (0.1% BSA, 1% Tween® 20) incubating each time for 10 minutes at room temp. The beads were then washed once with 1 ml PBS (0.1% BSA) and then stored in 1 ml PBS (0.05% sodium azide) at 4° C.

Proteinase K Digestion:

Conditions for the PK digestion of brain lysate: Brain homogenate was suspended in PBS buffer with or without non-ionic detergent. The total homogenate protein concentration was no more than 2.5 mg/mL. PK (Roche Diagnostics, IN, USA, Cat.# 1373196) was added to a final concentration of 50 ug/mL. Incubation was at 37 C for 0.5 to 1 hour. Digestion was stopped by adding Pefabloc® SC (Roche Diagnostics, IN, USA, Cat.# 1585916) to a final concentration of 4 mM.

Immunoprecipitation (IP), Non-reducing Electrophoresis and Immunoblot Detection of $PrP^{Sc}$:

Peptide conjugated magnetic beads were used to capture $PrP^{Sc}$ from brain homogenate by immunoprecipitation. The IP procedure consists of the following protocol: mix 50 uL peptide conjugated beads with PK treated or non-PK treated brain homogenate in a total of 1 mL IP buffer (3% Tween® 20 and 3% Igpal® CA-630 in PBS) and incubate at 25 C for 2.5 hours with rotation→Separate beads using MPC device and wash beads 3 times of 30 second vortexing with IP wash buffer (2% Tween®20 and 2% Igpal® CA-630 in PBS) →Elute captured $PrP^{Sc}$ by heating beads with NuPAGE® sample buffer for 10-15 minutes. The eluted sample from IP capture were loaded onto a 4-12% NuPAGE® Bis-Tris Gel (Invitrogen, CA, USA, Cat.# NP0302) and subjected to non-reducing electrophoresis at 200V for 45 minutes. The immunoblot procedure was performed as follows: transfer separated proteins in the gel to a 0.2um PVDF membrane (Invitrogen, Cat# LC2002) at 30V for 60 minutes→Block the membrane with Blocker™ Casein in TBS (0.05% Tween® 20) (Pierce Chemical Corp., IL, USA, Cat.# 37532) either at 25 C for 1 hour with shaking or at 4 C overnight.→As primary antibody, use 3F4 (Signet, MA, USA, Cat.# 9620-02) at 1:3000 dilution or 6H4 (Prionics AG, Switzerland, Cat.# 01-011) at 1:5000 dilution to detect $PrP^{Sc}$. Incubate the membrane with diluted primary antibody in 10% Blocker™ Casein in TBST buffer (25 mM Tri-Cl, 0.2M NaCl, 0.2% Tween® 20, pH 8.0) at 25 C for 1 hour with shaking.→Wash 3×5 minutes with TBST buffer with shaking.→Incubate membrane with horseradish peroxidase conjugated goat polyclonal anti-mouse IgG (H+L) (Jackson ImmunoResearch Laboratories, PA, USA, Cat.# 115-035-003) at 1:10,000 to 1:30,000 dilution in 50% Blocker™ Casein in TBST buffer at 25 C for 1 hour with shaking.→Wash 6×5 minutes with TBST buffer with shaking.→Add ECL chemiluminescence substrate (Amersham Biosciences, NJ, USA, Cat.# RPN2109) or SuperSignal® West Dura chemiluminescence substrate (Pierce) on membrane to develop for 5 minutes.→Take image by exposure either to Bio Max® MR-2 film (Kodak, NY, USA) or to the ChemiDoc™ Gel Documentation System (Bio-Rad, CA, USA).

Advantages.

The present invention uses peptide to capture $PrP^{Sc}$ by recognition of high affinity associated molecules in $PrP^{Sc}$ complex such as glycans, nucleic acid. Because the tight association of these molecules only to $PrP^{Sc}$ but not to $PrP^{C}$, the present invention provided a non-intrusive means for the detection of $PrP^{Sc}$ while no PK digestion or other protein modification procedure required. It is anticipated that the mild conditions will preserve the original structure and conformation of the pathogenic prion protein, thereby offering opportunity to determine the presence of true $PrP^{Sc}$ while minimizing the generation of $PrP^{Sc}$ due to harsh sample treatment.

The use of synthetic peptides offer advantages in that they display the binding specificity but can also be easily handled in direct coating to a solid phase as well as be conjugated to link to signal given reagents such as horseradish peroxidase (HRP), or to be adopted into other desired diagnosis assay format.

LITERATURE CITED

Aguzzi A, Fischer M B, (2001) Prion-Binding Activity in Serum and Plasma., US 20010053533A1

Appel T R, Dumpitak C, Matthiesen U, Riesner D. (1999) Prion rods contain an inert polysaccharide scaffold. Biol Chem 380(11):1295-306

Arnold, J E, Tipler C, Laszlo L, Hope J, Landon M, Mayer R J (1995) The abnormal isoform of the prion protein accumulates in late-endosome-like organelles in scrapie-infected mouse brain. J. Pathol. 176:403-411

Barnard G, Helmick B, Madden S, Gilbourne C and Patel R (2000) The measurement of prion protein in bovine brain tissue using differential extraction and DELFIA as a diagnostic test for BSE Luminescence 2000; 15:357-362

Belay E D (1999) Transmissible spongiform encephalopathies in humans. Annu. Rev. Microbiol. 53:283-314.

Biffiger K, Zwald D, Kaufmann L, Briner A, Nayki I, Purro M, Bottcher S, Struckmeyer T, Schaller O, Meyer R, Fatzer R, Zurbriggen A, Stack M, Moser M, Oesch B, Kubler E. (2002) Validation of a luminescence immunoassay for the detection of PrP(Sc) in brain homogenate. J Virol Methods 101(1-2):79-84.

Bolton D C (2001) Prions and proteins: distinguishing between conformations. The Lancet 358(9277):164-165

Brown P, Cathala F, Raubertas R F, Gajdusek D C, Castaigne P. (1987) The epidemiology of Creutzfeldt-Jakob disease: conclusion of a 15 year investigation in France and review of the world literature. Neurology 37:895-904.

Brown P. The risk of bovine spongiform encephalopathy ("mad cow disease") to human health. JAMA 1997; 278: 1008-1011

Bruce M E, Will R G, Ironside J W, McConnell I, Drummond D, Suttie A, McCardle L, Chree A, Hope J, Birkeft C, Cousens S, Fraser H and Bostock C J. (1997) Transmissions to mice indicate that 'new variant' CJD is caused by the BSE agent. Nature 389:498-501

Caughey B W, Dong A, Bhat K S, Ernst D, Hayes S F, Caughey, W. S. (1991) Secondary structure analysis of the scrapie-associated protein PrP27-30 in water by infrared spectroscopy. Biochemistry 30:7672-7680.

Caughey B and Kocisko D A. (2003) A nucleic-acid accomplice? Nature October 16; 425(6959):673-4

Chandler R, (1961) Encephalopathy in mice produced with scrapie brain material. Lancet 1:1378-1379

Cohen F E, Prusiner S B. (1998) Pathologic conformations of prion proteins. Annu Rev Biocem 67:793-819

Cordeiro Y, Machado F, Juliano L, Juliano M A, Brentani R R, Foguel D, Silva J L. (2001) DNA converts cellular prion protein into the beta-sheet conformation and inhibits prion peptide aggregation. J Biol Chem. 276(52):49400-9.

Cuillé J, Chelle P L (1936) La maladie dite tremblante du mouton est-elle inocuable? C. R. Acad. Sci. 203, 1552-1554

Deleault N D, Lucassen R W and Supaftapone S. (2003) RNA molecules stimulate prion protein conversion. Nature October 16; 425(6959):717-20

D'iaz-Nido J., Wandosell F. and Avila J (2002) Glycosaminoglycans and beta-amyloid, prion and tau peptides in neurodegenerative diseases. J Biol Chem July; 23(7):1323-32

FDA and CBER, U.S. Department of Health and Human Services (2001) IV. RECOMMENDATIONS FOR DONOR DEFERRAL in Guidance for Industry: Revised Preventive Measures to Reduce the Possible Risk of Transmission of Creutzfeldt-Jakob Disease (CJD) and Variant Creutzfeldt-Jakob Disease (vCJD) by Blood and Blood Products Ferguson N M, Ghani A C, Donnelly C A, Hagenaars T J, Anderson R M. (2002) Estimating the human health risk from possible BSE infection of the British sheep flock. Nature 415(6870):420-4

Fischer M B, Roeckl C, Parizek P, Schwarz H P, Aguzzi A, (2000) Binding of disease-associated prion protein to plasminogen. Nature 408:479-83.

Foster J D, Hope J, McConnell I, Bruce M, Fraser H. (1994) Transmission of bovine spongiform encephalopathy to sheep, goats, and mice. Ann N Y Acad Sci 724:300-3.

Gabizon R, McKinley M P, Groth D, Prusiner SB (1988). Immunoaffinity purification and neutralization of scrapie prion infectivity. Proc. Natl. Acad. Sci. USA 85, 6617-6621.

Gajdusek D C, Gibbs C J J, Alpers M P (1966) Experimental transmission of a kuru-like syndrome to chimpanzees. Nature 209:794-796

Gajdusek D C, (1977) Unconventional viruses and the origin and disappearance of kuru. Science 197:943-60

Gibbs C J J, Gajdusek D C, Asher D M, Alpers M P, Beck E, Daniel P M, Matthews W B (1968) Creutzfeldt-Jakob disease (spongiform encephalopathy): transmission to the chimpanzee. Science 161, 388-389

Gibbs C J Jr, Gajdusek D C, Amyx H. (1979) Strain variation in the viruses of Creutzfeldt-Jakob disease and kuru. In: Prusiner S B, Hadlow W J, editors. Slow transmissible diseases of the nervous system. Volume 2. New York: Academic Press; p. 87-110.

Hill A F, Zeidler M, Ironside J, Collinge J (1997) Diagnosis of new variant Creutzfeldt-Jakob disease by tonsil biopsy. Lancet 349(9045):99-100

Hillier C E, Salmon R L, Neal J W, Hilton DA. (2002) Possible underascertainment of variant Creutzfeldt-Jakob disease: a systematic study. J Neurol Neurosurg Psychiatry 72(3):304-9

Hines K L, Kulkarni A B, McCarthy J B, Tian H, Ward J M, Christ M, McCartney-Francis N L, Furcht L T, Karlsson S, Wahl S M. (1994) Synthetic fibronectin peptides interrupt inflammatory cell infiltration in transforming growth factor beta 1 knockout mice. Proc Natl Acad Sci USA May 24; 91(11):5187-91.

Holada K, Simak J, Vostal J G (2000) Transmission of BSE by blood transfusion. Lancent 356(9243): 1772

Hope J, Morton L J D, Farquhar C F, Multhaup G, Beyreuther K, Kimberlin R H (1986). The major polypeptide of scrapie-associated fibrils (SAF) has the same size, charge distribution and N-terminal protein sequence as predicted for the normal brain protein (PrP). EMBO J. 5, 2591-2597.

Horiuchi M, Caughey B, (1999) Specific binding of normal prion protein to the scrapie form via a localized domain initiates its conversion to the protease-resistant state. EMBO J 18(12):3193-203.

Horwich A L, Weissman J S (1997) Deadly Conformations-Protein Misfolding in Prion Disease. Cell, 89:499-510

Houston F (2000) Transmission of BSE by blood transfusion in sheep. Lancet 356(9234):999-1000

Hunter N, Foster J, Chong A, McCutcheon S, Parnham D, Eaton S, MacKenzie C, Houston F. (2002) Transmission of prion diseases by blood transfusion. J Gen Virol November; 83(Pt 11):2897-905

Jackson G S, Hosszu L L, Power A, Hill A F, Kenney J, Saibil H, Craven C J, Waltho J P, Clarke A R, Collinge J. (1999) Reversible conversion of monomeric human prion protein between native and fibrilogenic conformations. Science 283(5409): 1935-7.

Kellings K, Meyer N, Mirenda C, Prusiner S B, Riesner D. (1992). Further analysis of nucleic acids in purified scrapie prion preparations by improved return refocusing gel electrophoresis. J. Gen. Virol. 73, 1025-1029.

Kimberlin R H, Cole S, Walker C A. (1987) Temporary and permanent modifications to a single strain of mouse scrapie on transmission to rats and hamsters. J Gen Virol 68:1875-81.

Kimberlin R H, Walker C A, Fraser H. (1989) The genomic identity of different strains of mouse scrapie is expressed in hamsters and preserved on reisolation in mice. J Gen Virol 70:2017-25.

Klein T R, Kirsch D, Kaufmann R. and Riesner D (1998) Biol. Chem. 379:655-666

Korth C, Stierli B, Streit P, Moser M, Schaller O, Fischer R, Schulz-Schaeffer W, Kretzschmar H, Raeber A, Braun U, Ehrensperger F, Hornemann S, Glockshuber R, Riek R, Billeter M, Wuthrich K, Oesch B. (1997) Prion (PrP$^{Sc}$)-specific epitope defined by a monoclonal antibody. Nature 390(6655):74-7

Lasmézas C I, Deslys J P, Demaimay R, Adjou K T, Lamoury F, et al. (1996) BSE transmission to macaques. Nature 381:743-44

Luo Y, Gabriel J L, Wang F, Zhan X, Maciag T, Kan M, McKeehan W L. (1996) Molecular modeling and deletion mutagenesis implicate the nuclear translocation sequence in structural integrity of fibroblast growth factor-1. J Biol Chem. October 25; 271(43):26876-83.

Maissen M, Roeckl C, Markus G, Goldman W, Aguzzi A, (2001) Plasminogen binds to disease-associated prion protein of multiple species. Lancet 357:2026-8.

Manuelidis E E, Kim J H, Mericangas J R, Manuelidis L. (1985) Transmission to animals of Creutzfeldt-Jakob disease from human blood. Lancet 2:896-97

McBride P A, Wilson M I, eikelenboom P, Tunstall A, Bruce M E (1998) Heparan Sulfate Proteoglycan is Associated with Amyloid Plaques and Neuroanatomically Targeted PrP Pathology throughout the Incubation Period of Scrapie-Infected Mice. Experimental Neurol. 149:447-454

McGowan J P. (1922) Scrapie in sheep. Scott. J. Agric. 5:365-75

Meyer R K, McKinley M P, Bowman K A, Braunfeld M B, Barry R A, Prusiner S B (1986). Separation and properties of cellular and scrapie prion proteins. Proc. Natl. Acad. Sci. USA 83:2310-2314.

Mizuno K, Inoue H, Hagiya M, Shimizu S, Nose T, Shimohigashi Y, Nakamura T. (1994) Hairpin loop and second kringle domain are essential sites for heparin binding and biological activity of hepatocyte growth factor. J Biol Chem. January 14; 269(2):1131-6.

Moynagh J, Schimmel H, (1999) The evaluation of tests for the diagnosis of Transmissible Spongiform Encephalopathy in Bovines (8 Jul. 1999) http://europa.eu.int/comm/food/fs/bse/bse12-en.html.

Narang H K (2002) A critical review of the nature of the spongiform encephalopathy agent: prion theory versus virus theory. Exp Biol. Med. (Maywood) 227(1):4-19

O'Rourke K I, Baszler T V, Besser T E, Miller J M, Cutlip R C, Wells G A, et al. (2000) Preclinical diagnosis of scrapie by immunohistochemistry of third eyelid lymphoid tissue. J Clin Microbiol 38:3254-9.

Pan K M, Baldwin M, Nguyen J, Gasset M, Serban A, Groth D, Mehlhorn I, Huang Z, Fletterick R J, Cohen F E, Prusiner S B. (1993) Conversion of—helices into—sheets features in the formation of the scrapie prion proteins. Proc. Natl. Acad. Sci. USA 90:10962-10966

Paramithiotis E et al (2003) A prion protein epitope selective for the pathologically misfolded conformation Nat Med July; 9(7):893-9

Parizek P, Roeckl C, Weber J, Flechsig E, Aguzzi A, Raeber A J. (2001) Similar turnover and shedding of the cellular prion protein in primary lymphoid and neuronal cells. J Biol Chem 276:44627-44632.

Pattison I (1957) Transmission of scrapie to the goat. Lancet 272:104-105.

Prusiner S B, Novel proteinaceous infectious particles cause scrapie. Science (1982) 216:136-44

Raymond G J et al. (2000) Evidence of a molecular barrier limiting susceptibility of humans, cattle and sheep to chronic wasting disease. EMBO J September 1; 19(17): 4425-30

Safar J, Wille H, Itri V, Groth D, Serban H, Torchia M, Cohen F E, Prusiner S B. (1998) Eight prion strains have PrP(Sc) molecules with different conformations. Nat. Med. 4(10): 1157-65

Schaller O, Fatzer R, Stack M, Clark J, Cooley W, Biffiger K, Egli S, Doherr M, Vandevelde M, Heim D, Oesch B, Moser M. (1999) Validation of a western immunoblotting procedure for bovine PrP(Sc) detection and its use as a rapid surveillance method for the diagnosis of bovine spongiform encephalopathy (BSE). Acta Neuropathol (Berl) 98(5):437-43.

Shaked G M, Meiner Z, Avraham I, Taraboulos A, Gabizon R (2001a) Reconstitution of Prion Infectivity from Solubilized Protease-resistant PrP and Nonprotein Components of Prion Rods. J. Biol. Chem. 276(17):14324-14328

Shaked G M, Shaked Y, Kariv-Inbal Z, Halimi M, Avraham I, Gabizon R, (2001b) A Protease-resistant Prion Protein Isoform Is Present in Urine of Animals and Humans Affected with Prion Diseases J. Biol. Chem., 276(34):31479-82

Shyng S L, Heuser J E, Harris D A. (1994) Aglycolipid-anchored prion protein is endocytosed via clathrin-coated pits. J. Cell Biol. 125:1239-50

Small D H, Nurcombe V, Reed G, Clarris H, Moir R, Beyreuther K, Masters C L. (1994) A heparin-binding domain in the amyloid protein precursor of Alzheimer's disease is involved in the regulation of neurite outgrowth. J. Neurosci. April; 14(4):2117-27

Snow A D (1990) Immunolocalization of heparan sulfate proteoglycans to the prion protein amyloid plaques of Gerstmann-Straussler syndrome, Creutzfeldt-Jakob disease and scrapie. Lab Invest. 63(5):601-1

Soeda S, Ohki H, Shimeno H, Nagamatsu A (1989) Further characterization of the binding of plasminogen to heparin: evidence for the involvement of lysine residues. Biochim Biophys Acta. November 9; 999(1):29-35.

Swietnicki W, Morillas M, Chen S G, Gambetti P, Surewicz W K. (2000) Aggregation and fibrillization of the recombinant human prion protein huPrP90-231. Biochemistry 39(2):424-31.

Taraboulos A, Serban D, Prusiner S B. (1990) Scrapie prion proteins accumulate in the cytoplasm of persistently infected cultured cells. J. Cell. Biol. 110:2117-32

Tateishi J. (1985) Transmission of Creutzfeldt-Jakob disease from human blood and urine into mice. Lancet 2:1074

Telling G C, Scott M, Mastrianni J, Gabizon R., Torchia M, Cohen F E, DeArmond S J, Prusiner S B (1995). Prion propagation in mice expressing human and chimeric PrP transgenes implicates the interaction of cellular PrP with another protein. Cell 83:79-90.

Valleron A J, Boelle P Y, Will R, Cesbron J Y. (2001) Estimation of epidemic size and incubation time based on age characteristics of vCJD in the United Kingdom. Science 294(5547):1726-8

Wadsworth J D, Joiner S, et al. (2001) Tissue distribution of protease resistant prion protein in variant Creutzfeldt-Jakob disease using a highly sensitive immunoblotting assay. Lancet 358(9277):171-80

Warner R G, Hundt C, Weiss S, Turnbull J E (2002) Identification of the heparan sulfate binding sites in the cellular prion protein. J Biol Chem. May 24; 277(21):18421-30

Wells G A H, Scott A C, Johnson C T, Gunning R F, Hancock R D, et al. (1987) A novel progressive spongiform encephalopathy in cattle. Vet. Rec. 31:419-20

Williams E S, Young S. (1980) Chronic wasting disease of captive mule deer: a spongiform encephalopathy. J. Wildl. Dis. 16:89-98

Wong C, Xiong L W, Horiuchi M, Raymond L, Wehrly K, Chesebro B, Caughey B (2001) Sulfated glycans and elevated temperature stimulate PrPSc-dependent cell-free formation of protease-resistant prion protein EMBO J 20(3):377-386

Woods A. McCarthy J B, Furcht L T, Couchman J R. (1993) A synthetic peptide from the COOH-terminal heparin-binding domain of fibronectin promotes focal adhesion formation. Mol Biol Cell. June; 4(6):605-13

Yoshida I, Tashiro K, Monji A, Nagata i, Hayashi Y, Mitsuyama Y, Tashiro N. (1999) Identification of a heparin binding site and the biological activities of the laminin alpha1 chain carboxy-terminal globular domain. J Cell Physiol. April; 179(1):18-28.

I claim:

1. A method for detection of PrP$^{Sc}$ comprising:
   first contacting a sample with a peptide consisting of an amino acid sequence selected from the group consisting of: SEQ ID NO:1: WQPPRARI; SEQ ID NO:2: NWCKRGRKQCKTH; SEQ ID NO:3: NYKKPKL; SEQ ID NO:5: YRGYRGYRGYRG; SEQ ID NO:6: YRGRYGYKGKYGYRG; SEQ ID NO:7: AQKKDGKKRKRSRKESYSIYV; SEQ ID NO:8: ARTKQTARKSTGGKSPRKQLA; and SEQ ID NO:9: SGRGKGGKGLGKGGAKRHRKVLR; and
   then detecting PrP$^{Sc}$ with a labeled prion specific antibody, wherein the peptide specifically captures PrP$^{Sc}$ and the labeled prion specific antibody detects the captured PrP$^{Sc}$.

2. A method for detection of PrP$^{Sc}$ comprising:
   first contacting a sample with a prion specific antibody; and
   then detecting PrP$^{Sc}$ with a labeled peptide consisting of an amino acid sequence selected from the group consisting of: SEQ ID NO:1: WQPPRARI; SEQ ID NO:2: NWCKRGRKQCKTH; SEQ ID NO:3: NYKKPKL; SEQ ID NO:5: YRGYRGYRGYRG; SEQ ID NO:6: YRGRYGYKGKYGYRG; SEQ ID NO:7: AQKKDGKKRKRSRKESYSIYV; SEQ ID NO:8: ARTKQTARKSTGGKSPRKQLA; and SEQ ID NO:9: SGRGKGGKGLGKGGAKRHRKVLR; wherein the prion specific antibody captures PrP$^{C}$ and PrP$^{Sc}$ and the labeled peptide specifically detects the captured PrP$^{Sc}$.

3. An immunoassay for detecting PrP$^{Sc}$ comprising:
   providing a solid support having bound thereto a peptide consisting of an amino acid sequence selected from the group consisting of: SEQ ID NO:1: WQPPRARI; SEQ ID NO:2: NWCKRGRKQCKTH; SEQ ID NO:3: NYKKPKL; SEQ ID NO:5: YRGYRGYRGYRG; SEQ ID NO:6: YRGRYGYKGKYGYRG; SEQ ID NO:7: AQKKDGKKRKRSRKESYSIYV; SEQ ID NO:8: ARTKQTARKSTGGKSPRKQLA; and SEQ ID NO:9: SGRGKGGKGLGKGGAKRHRKVLR;

contacting the solid support with a sample;

washing the support to remove any unbound sample;

contacting the solid support with a labeled prion specific antibody; and carrying out a detection step to determine if PrP$^{Sc}$ are bound to the solid support, wherein the peptide specifically captures PrP$^{Sc}$ and the labeled prion specific antibody detects the captured PrP$^{Sc}$.

4. An immunoassay for detecting PrP$^{Sc}$ comprising:

providing a solid support having bound thereto a prion specific antibody;

contacting the solid support with a sample;

washing the support to remove any unbound sample;

contacting the solid support with a labeled peptide consisting of an amino acid sequence selected from the group consisting of SEQ ID NO:1: WQPPRARI; SEQ ID NO:2: NWCKRGRKQCKTH; SEQ ID NO:3: NYKKPKL; SEQ ID NO:5: YRGYRGYRGYRG; SEQ ID NO:6: YRGRYGYKGKYGYRG; SEQ ID NO:7: AQKKDGKKRKRSRKESYSIYV; SEQ ID NO:8: ARTKQTARKSTGGKSPRKQLA; and SEQ ID NO:9: SGRGKGGKGLGKGGAKRHRKVLR; and carrying out a detection step to determine if PrP$^{Sc}$ are bound to the solid support, wherein the prison specific antibody captures PrP$^{C}$ and PrP$^{Sc}$ and the labeled peptide specifically detects the captured PrP$^{Sc}$.

* * * * *